US010315980B2

(12) United States Patent
Song et al.

(10) Patent No.: US 10,315,980 B2
(45) Date of Patent: Jun. 11, 2019

(54) HETEROGENEOUS CATALYST FOR PREPARING ACRYLIC ACID, AND ACRYLIC ACID PREPARATION METHOD USING SAME

(71) Applicants: LG Chem, Ltd., Seoul (KR); Korea Advanced Institute of Science and Technology, Daejeon (KR)

(72) Inventors: Dongsu Song, Daejeon (KR); Daesung Kim, Daejeon (KR); Wonjae Lee, Daejeon (KR); Yongjin Choe, Daejeon (KR); Hyunjoo Lee, Daejeon (KR); Minsu Kim, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

(21) Appl. No.: 15/744,687

(22) PCT Filed: Aug. 24, 2016

(86) PCT No.: PCT/KR2016/009388
§ 371 (c)(1),
(2) Date: Jan. 12, 2018

(87) PCT Pub. No.: WO2017/039218
PCT Pub. Date: Mar. 9, 2017

(65) Prior Publication Data
US 2018/0201569 A1    Jul. 19, 2018

(30) Foreign Application Priority Data

Sep. 1, 2015   (KR) .................. 10-2015-0123840

(51) Int. Cl.
| | |
|---|---|
| *C07C 67/40* | (2006.01) |
| *C07C 67/48* | (2006.01) |
| *C07C 67/62* | (2006.01) |
| *C07C 69/54* | (2006.01) |
| *B01J 37/34* | (2006.01) |
| *B01J 23/52* | (2006.01) |
| *B01J 37/03* | (2006.01) |
| *B01J 37/16* | (2006.01) |
| *B01J 23/66* | (2006.01) |
| *B01J 37/02* | (2006.01) |
| *B01J 35/02* | (2006.01) |

(52) U.S. Cl.
CPC .............. *C07C 67/40* (2013.01); *B01J 23/52* (2013.01); *B01J 23/66* (2013.01); *B01J 35/023* (2013.01); *B01J 37/0211* (2013.01); *B01J 37/031* (2013.01); *B01J 37/16* (2013.01); *B01J 37/34* (2013.01); *C07C 67/48* (2013.01); *C07C 67/62* (2013.01); *C07C 69/54* (2013.01)

(58) Field of Classification Search
CPC .......... C07C 67/40; C07C 69/54; B01J 23/52; B01J 23/66; B01J 35/023

See application file for complete search history.

(56) References Cited

U.S. PATENT DOCUMENTS

| | | | |
|---|---|---|---|
| 3,156,735 A | 11/1964 | Armstrong | |
| 4,107,204 A | 8/1978 | Murib | |
| 4,552,860 A | 11/1985 | Murib | |
| 4,792,620 A * | 12/1988 | Paulik | ................. B01J 31/0231 |
| | | | 560/232 |
| 6,303,537 B1 | 10/2001 | Wang et al. | |
| 6,825,149 B2 | 11/2004 | Khanmamedova | |
| 7,910,771 B2 | 3/2011 | Dubois et al. | |
| 8,168,562 B2 | 5/2012 | Augustine | |
| 2009/0292086 A1 | 11/2009 | Shin et al. | |
| 2013/0142720 A1* | 6/2013 | Chen | ...................... B01J 37/024 |
| | | | 423/245.1 |
| 2013/0303801 A1 | 11/2013 | Ueda et al. | |
| 2013/0333362 A1 | 12/2013 | Phillips et al. | |
| 2015/0080604 A1 | 3/2015 | Lensbouer | |
| 2015/0361021 A1 | 12/2015 | Kim et al. | |
| 2016/0096170 A1 | 4/2016 | Kim et al. | |
| 2016/0122272 A1 | 5/2016 | Lee et al. | |

FOREIGN PATENT DOCUMENTS

| | | |
|---|---|---|
| EP | 0602602 A1 | 6/1994 |
| FR | 2771310 A1 | 5/1999 |
| GB | 2508511 A | 6/2014 |
| JP | H11-221463 A | 8/1999 |
| KR | 1999-0087789 A | 12/1999 |
| KR | 10-20090057612 A | 6/2009 |
| KR | 10-0986898 B1 | 10/2010 |

(Continued)

OTHER PUBLICATIONS

Falleta et al (Royal Society of Chemistry, Faraday Discussions, Enhanced performance of the catalytic conversion of allyl alcohol to 3-hydroxypropionic acid using bimetallic gold catalysts, 2009, 2, pp. 57-58. (Year: 2009).*
Norskov et al, Nature Chemistry, Towards the Computational Design of Solid Catalysts, 2009, 1, pp. 37-46. (Year: 2009).*
Falletta, et al., "Enhanced performance of the catalytic conversion of allyl alcohol to 3-hydroxypropionic acid using bimetallic gold catalysts", Faraday Discussions, vol. 152, pp. 367-379 (2011).
Zheng, et al., "Commodity chemicals derived from glycerol, an important biorefinery feedstock", Chemical Reviews, 108, 12, pp. 5253-5277 (2008).

(Continued)

*Primary Examiner* — Paul A Zucker
(74) *Attorney, Agent, or Firm* — Dentons US LLP

(57) ABSTRACT

The present disclosure relates to a catalyst used in the preparation of acrylic acid and acrylic acid preparation method using the same, and more specifically, discloses a catalyst capable of enhancing selectivity of acrylic acid and a production yield of acrylic acid when preparing acrylic acid from allyl alcohol using a heterogeneous catalyst including bimetallic alloy catalyst particles of gold and another metal, and an acrylic acid preparation method using the same.

8 Claims, 2 Drawing Sheets

(56) References Cited

FOREIGN PATENT DOCUMENTS

| KR | 10-20120021385 A | 3/2012 |
|---|---|---|
| KR | 10-20120102080 A | 9/2012 |
| KR | 10-20140048400 A | 4/2014 |
| KR | 10-20150006349 A | 1/2015 |
| KR | 10-20150021055 A | 2/2015 |
| KR | 10-20150032194 A | 3/2015 |
| KR | 10-20150144128 A | 12/2015 |
| KR | 10-20160041248 A | 4/2016 |
| WO | 97/33690 | 9/1997 |
| WO | 2008/092115 A1 | 7/2008 |
| WO | 2011/075278 A1 | 6/2011 |
| WO | 2012/005348 A1 | 1/2012 |
| WO | 2013114330 A1 | 8/2013 |
| WO | 2014/209065 A1 | 12/2014 |

OTHER PUBLICATIONS

Della Pina, et al., "A green approach to chemical building blocks. The case of 3-hydroxypropanoic acid", Green Chem., 13, pp. 1624-1632 (2011).

Della Pina, et al., "Oxidation of Allyl Alcohol in the Presence of a Gold Catalyst: A Route to 3-Hydroxypropionic Acid", ChemSusChem, vol. 2, pp. 57-58 (2009).

* cited by examiner

[FIG. 1]
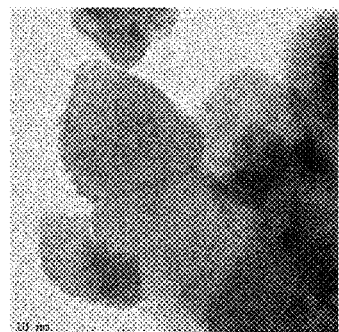
(a)
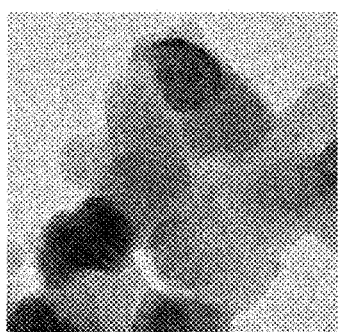
(b)
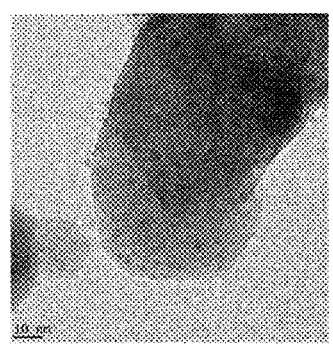
(c)
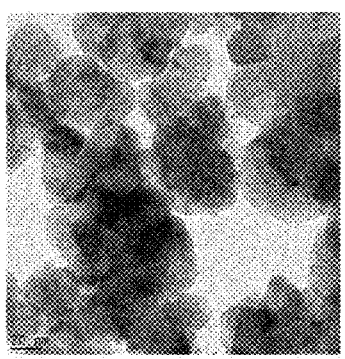
(d)
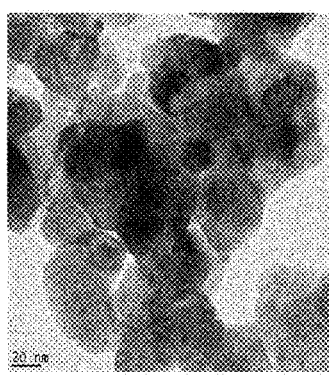
(e)
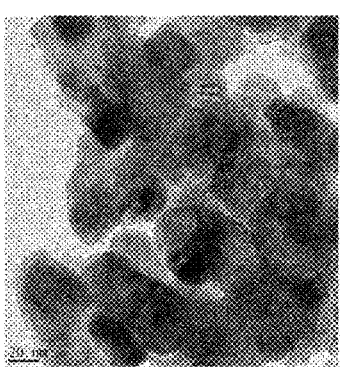
(f)

[FIG. 2]
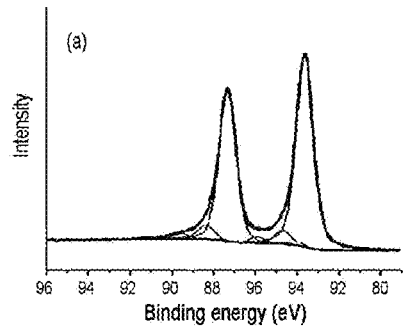
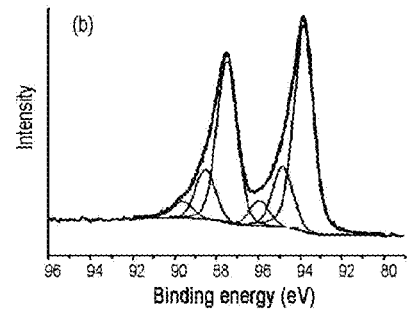
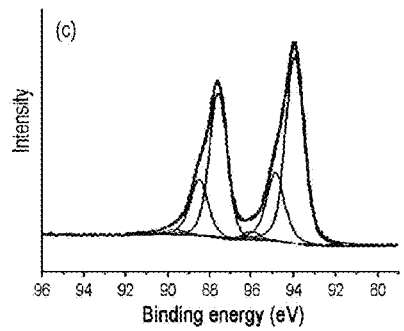
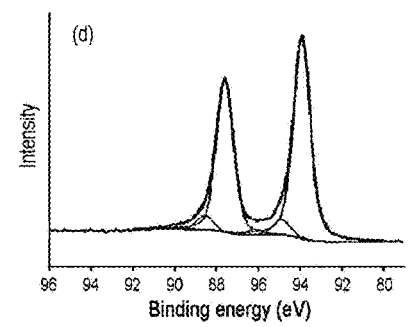
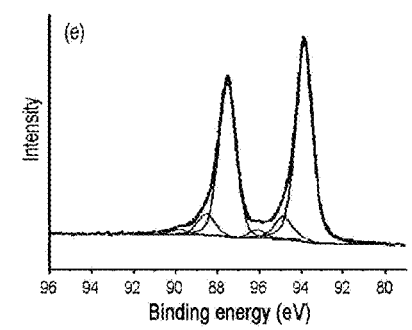
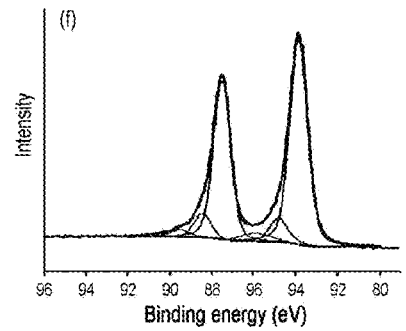

HETEROGENEOUS CATALYST FOR PREPARING ACRYLIC ACID, AND ACRYLIC ACID PREPARATION METHOD USING SAME

TECHNICAL FIELD

This application is a National Stage Application of International Application No. PCT/KR2016/009388, filed Aug. 24, 2016, and claims the benefit of Korean Patent Application No. 10-2015-0123840, filed Sep. 1, 2015, contents of which are incorporated herein by reference in their entirety for all purposes as if fully set forth below.

The present disclosure relates to a heterogeneous catalyst for preparing acrylic acid and a method for preparing acrylic acid from allyl alcohol using the same.

BACKGROUND ART

Traditionally, acrylic acid has been generally obtained based on fossil fuel as it is yielded from acrolein obtained from propylene. However, with environmental-friendly issues being treated importantly in the overall industrial environment relating to high oil prices and resource depletion problems, demands for developing environmental-friendly new processes based on biomass have increased in acrylic acid preparation as well, and this has been utilized in various forms across all industries.

For example, WO 2008/092115, an existing document in the art, describes allyl alcohol derived from glycerol, a byproduct of bio-diesel processes, and when acrylic acid is produced from the allyl alcohol, glycerol and bio-diesel can be economically utilized.

With such a recent trend, studies of various kinds on biomass-based acrylic acid process have been actively conducted. Particularly, proposes of various kinds have been made for various catalysts involving a 'glycerol-allyl alcohol-acrylic acid' formation path, one of representative biomass-based acrylic acid production reactions. For example, a series of proposes have been made in order to enhance a synthesis yield and synthesis reproducibility of each step, and in this regard, a method of enhancing a production yield of acrylic acid from allyl alcohol using a catalyst having a form including gold (Au) in a metal oxide support as a catalyst active site has been proposed.

With the catalyst, reproducibility and the like of reactions producing acrylic acid from allyl alcohol is enhanced and a production yield of the acrylic acid is enhanced by a maximum of half as well. However, in order to increase the industrial utility, higher level of acrylic acid selectivity and more enhanced acrylic acid production yield therefrom are still required.

PRIOR ART DOCUMENTS

Patent Documents

Korean Patent Application Laid-Open Publication No. 2015-0006349 (2015 Jan. 16), METHOD FOR PRODUCING ACRYLIC ACID FROM GLYCEROL

DISCLOSURE

Technical Problem

As a result of putting quite an effort and repeated studies to develop new catalysts in a more improved form, the inventors of the present disclosure have identified that, compared to a catalyst including only gold (Au), selectivity to acrylic acid and an acrylic acid production yield obtained therefrom are significantly enhanced when the catalyst further includes a different type of transition metal such as palladium (Pd) in a proper ratio, and have completed the present disclosure.

Accordingly, the present disclosure is directed to providing a new catalyst composition capable of increasing production efficiency of acrylic acid.

The present disclosure is also directed to providing a method for preparing acrylic acid from allyl alcohol using the catalyst.

Technical Solution

In view of the above, one embodiment of the present disclosure provides a heterogeneous catalyst for preparing acrylic acid in order to prepare acrylic acid from allyl alcohol, the bimetallic alloy catalyst represented by AuX (X=Pd, Ru, Rh, Os, Ir or Pt) deposited on a support.

Herein, the AuX catalyst has a size of 10 nm or less.

Another embodiment of the present disclosure provides a method for preparing acrylic acid from allyl alcohol by an oxidation reaction using the heterogeneous catalyst for preparing acrylic acid.

Herein, the oxidation reaction is carried out under the presence of one or more types of bases selected from the group consisting of NaOH, KOH, NaHCO$_3$, Na CO$_3$, KHCO$_3$, K$_2$CO$_3$ and CaCO$_3$.

In addition, the oxidation reaction is carried out by injecting oxygen or oxygen-including gas with a pressure of 1 bar to 6 bars.

Furthermore, the oxidation reaction is carried out at 30 to 100° C.

Advantageous Effects

Using the above-mentioned technical solution, the present disclosure provides a new catalyst composition capable of increasing production efficiency of acrylic acid produced from allyl alcohol, and a method for preparing the same. When using the new catalyst according to the present disclosure, commercial large-scale production becomes possible, which is capable of enhancing productivity of acrylic acid preparation from allyl alcohol.

In addition, the new catalyst of the present disclosure can be utilized in a method for preparing acrylic acid from allyl alcohol prepared from glycerol, a biomass-derived material, and therefore, has an advantage of being used in an environmental-friendly way such as enhancing bio-diesel utilization efficiency.

DESCRIPTION OF DRAWINGS

FIG. 1 shows transmission electron microscope images of a heterogeneous catalyst prepared according to a preparation method of the present disclosure.

FIG. 2 shows data of analysis results according to X-ray photoelectron spectroscopy (XPS) on a heterogeneous catalyst prepared according to a preparation method of the present disclosure.

MODE FOR DISCLOSURE

Acrylic acid may be prepared in various ways. The present disclosure uses a method having a reaction path from allyl alcohol to acrylic acid with the allyl alcohol as a starting material. Herein, in order to increase a conversion of the allyl alcohol to the acrylic acid and a yield of the acrylic acid, a catalyst including a specific composition is used in the present disclosure.

Heterogeneous Catalyst for Preparing Acrylic Acid

Activity of a catalyst directly affects a conversion from allyl alcohol to acrylic acid and an acrylic acid production yield, and the present disclosure uses a catalyst including a specific composition in order to increase the conversion and the production yield.

The catalyst according to the present disclosure is a heterogeneous catalyst, and uses a supported metal catalyst. Herein, as the supported metal catalyst for the heterogeneous catalyst, a bimetallic alloy catalyst alloyed with a different type of metal is used instead of a single metal such as gold (Au) used in the art.

Specifically, the bimetallic alloy catalyst is an Au—X-based catalyst, and herein, X is one or more types of transition metals selected from the group consisting of ruthenium (Ru), rhodium (Rh), palladium (Pd), osmium (Os), iridium (Ir) and platinum (Pt), and more preferably, palladium (Pd) is used.

A molar ratio of the Au and the X may be diversely controlled from 0.5:1 to 40:1, however, the range is preferably from 20:1 to 30:1 to increase a yield of acrylic acid prepared from allyl alcohol. Particularly, when a molar ratio of the Au:X deposited to the support of the bimetallic alloy catalyst is in the above-mentioned preferred range, the yield of acrylic acid as a produced major product may be 50% or greater and preferably 60% or greater.

According to preferred embodiments of the present disclosure, an Au—Pd catalyst as the bimetallic alloy catalyst and an Au catalyst are used, and these catalysts may all be used in the acrylic acid preparation, however, in terms of activity, the Au—Pd catalyst has more superior activity compared to the Au catalyst making it possible to prepare acrylic acid in a high yield in a short period of time.

Together with the bimetallic alloy catalyst composition, particle sizes are also one of important parameters in catalyst activity.

As sizes of the bimetallic alloy catalyst particles are smaller, catalyst activity increases, and herein, a contact area with reactants increases as particle sizes are more uniform resultantly increasing a conversion from allyl alcohol to acrylic acid, and as a result, an overall process time may be reduced.

Specifically, the Au—X-based bimetallic alloy catalyst has a particle size range of 10 nm or less, preferably 5 nm or less, and more preferably 3 nm or less, and in the above-mentioned range, the yield of acrylic acid as a major product reaches 50% or greater and preferably 60% or greater, which is more effective.

Moreover, in the heterogeneous catalyst according to the present disclosure, the support (carrier) on which the bimetallic alloy catalyst is deposited performs a role of supporting and dispersing the bimetallic alloy catalyst and thereby increasing surface areas thereof, stabilizing the catalyst by preventing a sintering phenomenon, and lowering a price of the bimetallic alloy catalyst. The support does not have activity itself, but affects catalyst activity with the above-mentioned functions, and a difference in the catalyst activity becomes large depending on the degree of metal catalyst loading even when the same composition is used, and therefore, selection of the support needs to be considered as very important.

Types of the usable support may include one or more types selected from the group consisting of activated carbon, titanium oxide ($TiO_2$), aluminum oxide ($Al_2O_3$), silicon oxide ($SiO_2$), zinc oxide ($ZnO_2$), zirconium oxide ($ZrO_2$), manganese oxide ($MnO_2$), iron oxide ($Fe_2O_3$), vanadium oxide ($V_2O_5$), tin oxide ($SnO_2$), tungsten oxide ($WO_3$) and cerium oxide ($CeO_2$), and more preferably, may be cerium oxide ($CeO_2$) or a composite oxide including cerium oxide.

In addition, a specific surface area, a pore volume and an average pore size of the support are required for a high catalyst loading amount, and the support preferably has a specific surface area of 1 $m^2/g$ or greater.

When using the support, a heterogeneous catalyst having a loading amount of 5% by weight or less and preferably 0.0001% by weight to 5% by weight may be prepared. It is advantageous as the loading amount increases, however, reproducibility, physical stability, costs, catalyst activity, selectivity and the like need to be considered as well when used in a production line. When the loading amount is less than the above-mentioned range, a sufficient level of heterogeneous catalyst activity is difficult to secure, and the loading amount of greater than the above-mentioned range reduces catalyst stability as well as being difficult to obtain, and therefore, the amount is properly used in the above-mentioned range.

A method for preparing the heterogeneous catalyst according to the present disclosure is not particularly limited. However, the heterogeneous catalyst is preferably prepared through preparing a bimetallic alloy catalyst and then depositing the bimetallic alloy catalyst on a support.

Specifically, the heterogeneous catalyst is prepared through (a) preparing a precursor solution including a transition metal precursor, a gold precursor and a basic compound;

(b) preparing a bimetallic alloy catalyst using a reduction reaction; and (c) preparing a supported bimetallic alloy catalyst by adding a support to a liquid dispersion in which the bimetallic alloy catalyst is dispersed, and mixing the result.

Hereinafter, each step will be described in detail.

First, a transition metal precursor, a gold precursor and a basic compound are mixed to prepare a precursor solution (step a).

The metal precursor may use any precursor capable of being converted to a metal catalyst by a reduction reaction, and may be alkoxide, acetyl acetate, nitrate, oxalate, halide, cyanide and the like including a metal, and preferably, a halide is used. As one example, when Pd is used, $PdCl_2$, $(NH_4)_2PdCl_4$, $Pd(NO_3)_2$, $Pd(NH_3)_2Cl_2$, $Pd(C_2H_3O_2)_2$ and the like may be used as the precursor, and most preferably, $PdCl_2$ is used.

As the gold precursor, $HAuCl_4$, $HAuCl_4.3H_2O$, $HAuCl_4.4H_2O$, $AuCl_3$, $AuCl$ and the like may be used, and preferably, $HAuCl_4$ is used.

The basic compound plays a role of converting Cl of the gold ligand to OH. Gold in an oxidized state is adequately reduced to a metal state therethrough under a catalyst synthesis condition, and when gold in an oxidized state and a metal state have an adequate ratio (approximately 30% of oxidized state and approximately 70% of metal state), an acrylic acid production yield is enhanced.

As the basic compound, one type selected from the group consisting of NaOH, KOH, $NaHCO_3$, $Na_2CO_3$, $KHCO_3$, $K_2CO_3$ $CaCO_3$ and combinations thereof may be preferably used, and more preferably, NaOH may be used. The basic compound may be included in 4 parts by weight to 15 parts by weight and preferably in 5 parts by weight to 8 parts by weight with respect to 100 parts by weight of the precursor solution. When the basic compound is included in less than 4 parts by weight, there may be a problem in that the catalyst reaction does not occur normally. When the basic compound is greater than 15 parts by weight, a problem of damaging the catalyst may occur, and therefore, the above-mentioned range is preferred.

The precursor solution may be prepared by introducing the transition metal precursor, the gold precursor and the basic compound to a solvent or a liquid dispersion at once, or mixing the transition metal precursor and the basic compound in advance, and then slowly dropping the mixture to the gold precursor.

The precursor solution is prepared by dissolving these metal precursors and basic compound in a solvent, and as the solvent, water, alcohols, ethers, ketones and aromatics may be used, and particularly water, alcohols or mixtures of water and alcohols are preferred.

Next, a bimetallic alloy catalyst is prepared by carrying out a reduction reaction of the precursor solution prepared in the step a (step b).

As for the reduction reaction, an alloying reaction of metal ions in the precursor solution takes place, and as the condition herein, the reaction is carried out for 5 minutes to 12 hours and preferably for 30 minutes to 3 hours at 30° C. to 200° C. and preferably at 80° C. to 140° C. The temperature and the time are sufficient conditions for the reduction reaction. Since the reaction is carried out under a reflux condition, the temperature range may change depending on the type of the solvent. In addition, the reaction is carried out under vacuum as necessary in order to enhance the reaction rate.

A bimetallic alloy catalyst is prepared through such a reduction reaction, and the particles have sizes of 10 nm or less as described above.

Next, a supported heterogeneous bimetallic alloy catalyst is prepared by adding a support to a liquid dispersion in which the bimetallic alloy catalyst is dispersed, and mixing the result (step c).

A method of separating the bimetallic alloy catalyst particles in the liquid dispersion and depositing the particles on a support, or a method of impregnating the liquid dispersion itself on a support may be used, and the method is not particularly limited in the present disclosure.

Prior to impregnating the bimetallic alloy catalyst-dispersed liquid dispersion, impurities inside the support are removed by calcinating the support for 10 hours to 24 hours and preferably for 20 hours to 24 hours at 100° C. to 700° C. and preferably at 300° C. to 500° C. under air or inert gas to use the support. Through such calcination, effects of having no oxygen vacancy on the metal oxide surface and greatly enhancing catalyst recyclability by relatively further stabilizing a gold active phase in the catalyst are obtained. When the temperature is lower than the above-mentioned range, the metal oxide surface is not sufficiently oxidized causing a problem of oxygen vacancy being still present, and the temperature being higher than the above-mentioned range may cause a problem of damaging a crystal structure of the metal oxide, and therefore, the above-mentioned range is preferred. In addition, when the calcination time is less than 10 hours, the metal oxide surface is not sufficiently oxidized causing a problem of oxygen vacancy being still present, and the time being longer than 24 hours may cause a problem of damaging a crystal structure of the metal oxide, and therefore, the above-mentioned range is preferred.

The deposition of the bimetallic alloy catalyst on a support may be carried out using a wet impregnation method, a dry impregnation method, a vacuum impregnation method, or spray drying or extrusion drying of slurry-type mixture, however, the method is not limited thereto. In the examples of the present disclosure, the deposition is carried out by adding a support to the bimetallic alloy catalyst liquid dispersion and mixing the result.

Such deposition may be carried out once or more, that is, repeated several times, so as to have a target level of loading amount, and as necessary, ultrasonic waves or heat may be applied, or stirring may be carried out.

The ultrasonic waves may have a frequency of 10 kHz to 300 kHz and preferably 20 kHz to 60 kHz. The ultrasonic wave frequency being more than 300 kHz may have a problem of causing damages on the bimetallic alloy catalyst particles due to high cavitation strength, and the frequency being less than 10 kHz may have a problem of reducing reproducibility since the ultrasonic treatment effect becomes weak. The ultrasonic treatment may be carried out for 3 minutes to 20 minutes and preferably for 5 minutes to 10 minutes, however, the time is not limited thereto. When the ultrasonic treatment is for less than 3 minutes, there may be a problem of bimetallic alloy catalyst dispersion being not sufficient, and the time being longer than 20 minutes may have a problem of causing damage on the structure of the bimetallic alloy catalyst.

After the ultrasonic treatment, solids are separated from the mixture, and prior to the separation of the solids, preferably the mixture is stirred for approximately 1 hour at a high temperature, that is, approximately 70° C., and then cooled at room temperature.

Through the above-mentioned steps, a supported heterogeneous bimetallic alloy catalyst is collected after separation and drying.

The drying may be carried out using an atmospheric drying method or a vacuum drying method. For example, in the atmospheric drying method, the drying is carried out for 2 hours to 72 hours and preferably for 5 hours to 48 hours at room temperature to 200° C. and preferably at room temperature to 150° C. under atmospheric pressure.

A heterogeneous catalyst prepared using such a preparation method has advantages of exhibiting excellent synthesis reproducibility and durability, and is preferably used in preparing acrylic acid from allyl alcohol.

Method for Preparing Acrylic Acid from Allyl Alcohol

The present disclosure provides a method for preparing acrylic acid from allyl alcohol by an oxidation reaction using the heterogeneous catalyst for preparing acrylic acid provided above.

The allyl alcohol used as a starting material is not particularly limited as long as it is capable of being used in acrylic acid preparation. As one example, the allyl alcohol may be used in a concentrated form or in a mixture solution form with water and the like, and preferably, allyl alcohol having purity of 60% to 99.9% may be used. In addition, when necessary, the allyl alcohol may be prepared using a method described in Korean Patent Application Laid-Open Publication No. 2015-0006349.

Herein, a reactor is not particularly limited in the present disclosure, and any one reactor selected from the group consisting of known batch reactors, semi-batch reactors, continuous stirred tank reactors, plug flow reactors, fixed bed reactors and fluidized bed reactors, or a mixed reactor linking two or more thereof may be used.

The method and the order of introducing the allyl alcohol, the heterogeneous catalyst and an oxidizing gas are not particularly limited, and various methods of introduction such as a method introducing these all together into a reactor, a method of continuous introducing these, and a method of introducing some of these into a reactor and continuously introducing the rest into the reactor may be used, and any method may be used. In one embodiment of the present disclosure, the heterogeneous catalyst is introduced to a reactor first, and then allyl alcohol is introduced thereto consecutively, and an oxidizing gas is continuously supplied thereto.

The oxidation reaction takes place as shown in Reaction Formula 1, and acrylic acid is produced as a major product, and 3-hydroxypropionic acid and glyceric acid are produced as minor products.

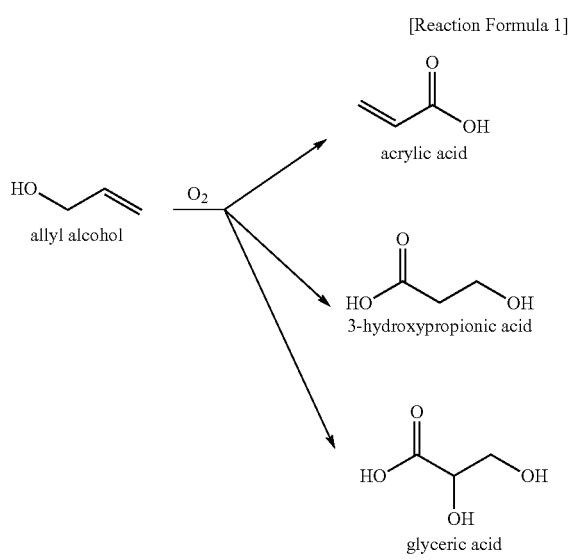

[Reaction Formula 1]

In Reaction Formula 1, when the heterogeneous catalyst proposed in the present disclosure is used, 100% of allyl alcohol participates in the oxidation reaction and is converted to acrylic acid in a short period of time, and a yield of the acrylic acid is identified to be high as well.

The oxidation reaction is carried out under the presence of a base, and the base capable of being used herein is not particularly limited in the present disclosure, and bases known in the art may be used. As one example, one type selected from the group consisting of NaOH, KOH, $NaHCO_3$, Na $CO_3$, $KHCO_3$, $K_2CO_3$ $CaCO_3$ and combinations thereof may be used as the base.

The base is preferably introduced in a molar ratio of 1 to 10 and more preferably introduced in a molar ratio of 3 to 6 based on 1 mol of the allyl alcohol. The amount of the basic compound introduced affects a conversion of the allyl alcohol, and yield and selectivity of the acrylic acid, the 3-hydroxypropionic acid (3-HPA) and the glyceric acid. In addition, the acid-type products including the acrylic acid and the 3-hydroxypropionic acid among the products may be produced in a salt form due to the addition of the basic compound.

In the present disclosure, an oxidative gas for the oxidation reaction may be oxygen or oxygen-including gas. The partial pressure of the oxidative gas may be arbitrarily determined outside the range of combustion and the range of explosion considering the reactant concentration and the reaction temperature. The partial pressure of oxygen may be from 1 bar to 6 bars and preferably from 1 bar to 5 bars based on the gauge.

In addition, the oxygen-including gas among the oxidative gas may include oxygen in 10% by volume or greater, preferably in 60% by volume to 100% by volume, and more preferably in 90% by volume to 100% by volume. When the oxygen content is less than 60% by volume, there is a problem in that the oxidation reaction rate becomes very low.

The reaction temperature is not particularly limited as long as it is a condition carrying out the reaction in a liquid state, however, the temperature is from 10° C. to 120° C., preferably from 20° C. to 100° C. and more preferably from 30° C. to 90° C. When the temperature inside the reactor is lower than 10° C., the oxidation reaction rate to the acrylic acid greatly decreases, which results in the significant decrease of conversion of allyl alcohol, and when the temperature is higher than 120° C., a side reaction products (that is, glyceric acid, 3-hydroxypropionic acid) greatly increases due to the temperature raise causing a problem of greatly reducing selectivity.

Meanwhile, the reaction time is not particularly limited as long as it is a condition sufficiently converting the allyl alcohol, and as one example, the reaction time may be from 10 hours to 30 hours.

The acrylic acid obtained using the oxidation reaction is separated through known methods and then collected.

The acrylic acid prepared in this step is obtained in an acrylate (that is, acrylic acid salt) form, and an additional process for being converted to acrylic acid, that is, an ion-exchange process is carried out after the acidification process to obtain acrylic acid.

Herein, the acrylic acid separation process is not particularly limited in the present disclosure, and methods known in the art may be used. As one example, the separation process may be carried out through an extraction method, a crystallization method or a fractional distillation method.

As a solvent used in the extraction method, one or more types selected from among alcohols, aldehydes, ketones, ethers, esters, aromatic compounds and other organic solvents may be included, however, the solvent is not limited thereto.

As the crystallization method, a suspension crystallization method and a layer crystallization method may be used as a method of separation using a solubility difference in the mixture.

The fractional distillation method is a method of separation using a boiling point difference in a mixture, and may be operated under vacuum, atmospheric pressure and pressurization. In order to enhance separation efficiency, a solvent may be introduced. Reactive distillation may be used for carrying out reaction and separation at the same time.

Acrylic acid separated as above may be used in various fields as a raw material of organic synthesis materials.

In addition, the 3-hydroxypropionic acid produced in the above-mentioned step may be collected after being converted to acrylic acid by a dehydration reaction with a catalyst using a method described in Korean Patent Application Laid-Open Publication No. 2015-6349.

The acrylic acid prepared by the above-mentioned step is capable of being applied as a raw material of various chemical products.

EXAMPLE

Hereinafter, the present disclosure will be described in more detail with reference to examples, however, the scope of the present disclosure is not limited to the following examples, and it needs to be construed as that the examples are for illuminating the present disclosure.

Example 1: Preparation of Heterogeneous Catalyst and Preparation of Acrylic Acid (1) Preparation of $Au_3Pd_1/CeO_2$ Heterogeneous Catalyst 5 ml of distilled water and 12 mg of $HAuCl_4 \cdot 3H_2O$ (99.9%) were placed in a mixer and uniformly mixed for 10 minutes. 5 ml of the obtained mixture solution was introduced to a reactor, and 45 ml of distilled water was added thereto.

25 μl of $PdCl_2$ solution and 775 μl of 0.2 M NaOH were added to the reactor, and the result was stirred for 20 minutes at 800 rpm to prepare bimetallic alloy catalyst particles.

To a bimetallic alloy catalyst particle-dispersed solution, 200 mg of cerium oxide was added as a support, and the result was ultrasonic treated for 10 minutes, then stirred for 1 hour at 70° C., and then cooled again at room temperature for 1 hour to deposit the bimetallic alloy catalyst on the support.

The obtained supported catalyst was filtered and then washed, and dried for 4 days under vacuum in 80° C. to prepare a titled catalyst.

(2) Preparation of Acrylic Acid

Acrylic acid was prepared from allyl alcohol using the heterogeneous catalyst prepared in (1).

To a 100 mL reactor, 1.17 mL of allyl alcohol, the heterogeneous catalyst (molar ratio of allyl alcohol/bimetallic alloy catalyst=4000/1) prepared in (1), and an aqueous NaOH solution (NaOH 2.064 g, Dl water 17.24 mL) were injected. Herein, the molar ratio of NaOH/allyl alcohol was employed to be 3/1.

The result was uniformly dispersed by applying ultrasonic waves, oxygen gas was injected thereto with 3 bars after vacuuming the reactor, the temperature inside the reactor was raised to 50° C., and an oxidation reaction was carried out for hours, and acrylic acid obtained after terminating the reaction was purified through fractional distillation.

Example 2: Preparation of Heterogeneous Catalyst and Preparation of Acrylic Acid An experiment was carried out in the same manner as Example 1, except that the heterogeneous catalyst was prepared using a different molar ratio of Au and Pd, and using the same, acrylic acid was prepared from allyl alcohol.

Example 3: Preparation of Heterogeneous Catalyst and Preparation of Acrylic Acid An experiment was carried out in the same manner as Example 1, except that the heterogeneous catalyst was prepared using a different molar ratio of Au and Pd, and using the same, acrylic acid was prepared from allyl alcohol.

Example 4: Preparation of Heterogeneous Catalyst and Preparation of Acrylic Acid An experiment was carried out in the same manner as Example 1, except that the heterogeneous catalyst was prepared using a different molar ratio of Au and Pd, and using the same, acrylic acid was prepared from allyl alcohol.

Example 5: Preparation of Heterogeneous Catalyst and Preparation of Acrylic Acid An experiment was carried out in the same manner as Example 1, except that the heterogeneous catalyst was prepared using a different molar ratio of Au and Pd, and using the same, acrylic acid was prepared from allyl alcohol.

Example 6: Preparation of Heterogeneous Catalyst and Preparation of Acrylic Acid An experiment was carried out in the same manner as Example 1, except that the heterogeneous catalyst was prepared using a different molar ratio of Au and Pd, and using the same, acrylic acid was prepared from allyl alcohol.

Comparative Example 1: Preparation of Au Catalyst and Acrylic Acid (1) Preparation of $Au/CeO_2$ Catalyst 12 mg of $HAuCl_4 \cdot 3H_2O$ was dissolved in 50 ml of distilled water, and a pH of the solution was adjusted to 10 using an aqueous NaOH solution. After that, 200 mg of cerium oxide was dispersed into the solution as a support, and the result was ultrasonic treated for 10 minutes at 20 kHz. After that, the solution was kept for 1 hour at 70° C. to prepare a catalyst.

(2) Preparation of Acrylic Acid

Acrylic acid was prepared in the same manner as in Example 1, except that the $Au/CeO_2$ catalyst prepared in (1) was used as a catalyst.

Comparative Example 2: Preparation of Au Catalyst and Acrylic Acid (1) Preparation of $Au/CeO_2$ Catalyst A catalyst was prepared in the same manner as in Comparative Example 1 except that cerium oxide (1 g), the support, was placed in an alumina boat and then calcinated for 8 hours at 400° C. in a tube furnace to be used.

(2) Preparation of Acrylic Acid

Acrylic acid was prepared in the same manner as in Example 1, except that the $Au/CeO_2$ catalyst prepared in (1) was used as a catalyst.

Comparative Example 3: Preparation of Au Catalyst and Acrylic Acid (1) Preparation of $Au/CeO_2$ Catalyst 12 mg of $HAuCl_4 \cdot 3H_2O$ was dissolved in 50 ml of distilled water, and a pH of the solution was adjusted to 10 using an aqueous NaOH solution. After that, 200 mg of cerium oxide was dispersed into the solution as a support, and the result was ultrasonic treated for 10 minutes at 20 kHz. After that, the solution was kept for 9 hours at 70° C. to prepare a catalyst.

(2) Preparation of Acrylic Acid

Acrylic acid was prepared in the same manner as in Example 1, except that the $Au/CeO_2$ catalyst prepared in (1) was used as a catalyst.

Test Example 1: Physical Property Analysis on Heterogeneous Catalyst

Molar ratios of the catalysts prepared in the examples and the comparative examples were analyzed using an inductively coupled plasma (ICP) analysis, and the particle sizes were measured using a transmission electron microscope (TEM), and the obtained results are shown in the following Table 1 and FIG. 1.

TABLE 1

| Category | Heterogeneous Catalyst | Bimetallic Alloy Catalyst Au:Pd (ICP) Molar Ratio | Particle Size |
|---|---|---|---|
| Example 1 | $Au_3Pd_1/CeO_2$ | 0.7:1 | 1.5 ± 0.3 nm |
| Example 2 | $Au_9Pd_1/CeO_2$ | 3.4:1 | 1.6 ± 0.2 nm |
| Example 3 | $Au_{18}Pd_1/CeO_2$ | 15.3:1 | 2.1 ± 0.4 nm |
| Example 4 | $Au_{36}Pd_1/CeO_2$ | 26.5:1 | 2.6 ± 0.5 nm |
| Example 5 | $Au_{72}Pd_1/CeO_2$ | 29.7:1 | 2.8 ± 0.6 nm |
| Example 6 | $Au_{144}Pd_1/CeO_2$ | 36.7:1 | 2.9 ± 0.6 nm |
| Comparative Example 1 | $Au/CeO_2$ | 1:1 | 1.5 nm |
| Comparative Example 2 | $Au/CeO_2$ | 1:1 | 4 nm |
| Comparative Example 3 | $Au/CeO_2$ | 1:1 | 4 nm |

When referring to Table 1, it was seen that the bimetallic alloy catalysts prepared in the examples and the comparative examples had very small sizes of 5 nm or less.

Such particle sizes were able to be identified in detail through a TEM image analysis. FIG. 1 shows TEM images of the heterogeneous catalysts prepared in Examples 1 to 6, and shows TEM images of (a) the heterogeneous catalyst of Example 1, (b) the heterogeneous catalyst of Example 2 (c) the heterogeneous catalyst of Example 3, (d) the heterogeneous catalyst of Example 4, (e) the heterogeneous catalyst of Example 5 and (f) the heterogeneous catalyst of Example 6. When referring to FIG. 1, it was seen that, in the heterogeneous catalyst, the nm-level bimetallic alloy catalyst (Au—Pd, small particles) was uniformly supported in the large particles ($CeO_2$).

In addition, X-ray Photoelectron Spectroscopy (XPS) was performed in order to identify a binding state of Au and Pd, a bimetallic alloy catalyst forming the heterogeneous catalyst, and the obtained results are shown in FIG. 2.

FIG. 2 shows XPS images of the heterogeneous catalysts prepared in Examples 1 to 6, and shows XPS spectra of (a) the heterogeneous catalyst of Example 1, (b) the heterogeneous catalyst of Example 2, (c) the heterogeneous catalyst of Example 3, (d) the heterogeneous catalyst of Example 4, (e) the heterogeneous catalyst of Example 5 and (f) the heterogeneous catalyst of Example 6. When referring to FIG. 2, it was seen that the metals of Au and Pd of the bimetallic alloy catalyst were present in an alloyed state.

Test Example 2: Analyses on Allyl Alcohol Conversion and Acrylic Acid Yield

The conversion of the allyl alcohol and the yield of the acrylic acid prepared in Examples 1 to 6 and Comparative Examples 1 to 3 were calculated, and the results are compared and summarized in the following Table 2.

The conversion of the allyl alcohol and the yield of the acrylic acid were measured through a high performance liquid chromatography (HPLC) analysis. The conversion of the allyl alcohol is a molar ratio of the allyl alcohol consumed during the reaction with respect to the allyl alcohol before the reaction, and a 100% conversion means all the allyl alcohol participated in the reaction. In addition, glyceric acid and 3-hydroxypropionic acid (3-HPA) were produced as side-reaction materials of the oxidation reaction. The yield of each means a molar ratio of the produced material with respect to the allyl alcohol before the reaction.

TABLE 2

| Category | Conversion (%) of Allyl Alcohol | Yield (%) Acrylic Acid | 3-Hydroxypropionic Acid | Glyceric Acid |
|---|---|---|---|---|
| Example 1 | 100 | 20.3 | 6.6 | 5.1 |
| Example 2 | 100 | 23.7 | 3.7 | 3.1 |
| Example 3 | 100 | 30.1 | 7.2 | 6.9 |
| Example 4 | 100 | 58.7 | 10.9 | 2.2 |
| Example 5 | 100 | 60.1 | 21.3 | 0 |
| Example 6 | 100 | 46.8 | 23.7 | 0 |
| Comparative Example 1 | 100 | 50.7 | 29.6 | 2.8 |
| Comparative Example 2 | 100 | 50.4 | 29.6 | 2.6 |
| Comparative Example 3 | 100 | 51.1 | 30.1 | 2.9 |

When referring to Table 2, it was seen that the yield of the acrylic acid was high with a maximum of approximately 60% level when using the supported bimetallic alloy heterogeneous catalysts of Examples 1 to 6 according to the present disclosure.

When using the catalysts of Comparative Examples 1 to 3, the yield of the acrylic acid was high, however, the production yields of the 3-hydroxypropionic acid and the glyceric acid were relatively high with respect to the acrylic acid, and therefore, it was seen that selectivity of acrylic acid was low.

Particularly, it was seen that acrylic acid was capable of being produced in a selective yield when using the catalysts of Examples 4 to 6, and therefore, the result was most effective when a molar ratio of Au and Pd was in a range of 20:1 to 30:1.

The invention claimed is:

1. A heterogeneous catalyst for preparing acrylic acid from allyl alcohol, wherein the heterogeneous catalyst is a bimetallic alloy catalyst deposited on a cerium oxide support, wherein the bimetallic alloy catalyst has the following chemical formula: AuX, wherein X=Pd, and wherein the molar ratio of Au:X is from 20:1 to 40:1.

2. The heterogeneous catalyst for preparing acrylic acid of claim 1, wherein the bimetallic alloy catalyst has a particle size of 10 nm or less.

3. The heterogeneous catalyst for preparing acrylic acid of claim 1, wherein the bimetallic alloy catalyst is included in an amount of 5% by weight or less with respect to the total dry weight of the support.

4. A method for preparing acrylic acid from allyl alcohol, the method comprising an oxidation reaction of allyl alcohol in the presence of the heterogeneous catalyst of claim 1.

5. The method for preparing acrylic acid of claim 4, wherein the oxidation reaction is carried out in the presence of a base.

6. The method for preparing acrylic acid of claim 5, wherein the base is at least one selected from the group consisting of NaOH, KOH, $NaHCO_3$, $Na_2CO_3$, $KHCO_3$, $K_2CO_3$ and $CaCO_3$.

7. The method for preparing acrylic acid of claim 4, wherein the oxidation reaction is carried out by injecting oxygen or oxygen-including gas with a pressure of 1 bar to 6 bars.

8. The method for preparing acrylic acid of claim 4, wherein the oxidation reaction is carried out at 30° C. to 100° C.

\* \* \* \* \*

UNITED STATES PATENT AND TRADEMARK OFFICE
CERTIFICATE OF CORRECTION

PATENT NO. : 10,315,980 B2  
APPLICATION NO. : 15/744687  
DATED : June 11, 2019  
INVENTOR(S) : Dongsu Song et al.

Page 1 of 1

It is certified that error appears in the above-identified patent and that said Letters Patent is hereby corrected as shown below:

On the Title Page

The assignee data should read as below:  
(73) Assignee: LG CHEM, LTD. (Seoul, KR)  
KOREA ADVANCED INSTITUTE OF SCIENCE AND TECHNOLOGY (Daejeon, KR)

Signed and Sealed this  
Twenty-eighth Day of July, 2020

Andrei Iancu  
*Director of the United States Patent and Trademark Office*